(12) United States Patent
Jung

(10) Patent No.: US 11,585,774 B2
(45) Date of Patent: Feb. 21, 2023

(54) SOIL MOISTURE SENSOR AND OPERATING METHOD THEREOF

(71) Applicant: DAMOATECH CO., LTD., Seongnam-si (KR)

(72) Inventor: Hu Min Jung, Hanam-si (KR)

(73) Assignee: DAMOATECH CO., LTD., Seongnam-si (KR)

( * ) Notice: Subject to any disclaimer, the term of this patent is extended or adjusted under 35 U.S.C. 154(b) by 168 days.

(21) Appl. No.: 17/238,629

(22) Filed: Apr. 23, 2021

(65) Prior Publication Data

US 2021/0239641 A1 Aug. 5, 2021

Related U.S. Application Data

(63) Continuation of application No. PCT/KR2019/014124, filed on Oct. 25, 2019.

(30) Foreign Application Priority Data

Oct. 25, 2018 (KR) .......................... 10-2018-0128105
Sep. 27, 2019 (KR) .......................... 10-2019-0119988

(51) Int. Cl.
  *G01N 27/00* (2006.01)
  *G01N 27/22* (2006.01)
  *G01N 33/24* (2006.01)
(52) U.S. Cl.
  CPC ......... *G01N 27/223* (2013.01); *G01N 27/228* (2013.01); *G01N 33/24* (2013.01); *G01N 33/246* (2013.01)

(58) Field of Classification Search
  USPC .......................................... 324/634, 664, 682
  See application file for complete search history.

(56) References Cited

U.S. PATENT DOCUMENTS 4,909,070 A * 3/1990 Smith .................. G01N 27/225
              324/690
5,418,466 A   5/1995 Watson et al.
(Continued)

FOREIGN PATENT DOCUMENTS

EP  2 594 930 A1   5/2013
JP  3900395 B2    4/2007
(Continued)

*Primary Examiner* — Vincent Q Nguyen
(74) *Attorney, Agent, or Firm* — United One Law Group LLC; Kongsik Kim; Jhongwoo Peck

(57) ABSTRACT

Disclosed herein are a soil moisture sensor and an operating method thereof. The soil moisture sensor includes a first probe including a pair of first electrodes extending in a first direction; a first resonance circuit connected to the pair of first electrodes of the first probe through a pair of first ports, and configured such that a first AC signal is applied thereto; a second resonance circuit having the same impedance as the first resonance circuit, and configured such that a second AC signal having the same characteristics as the first AC signal while being a reference AC signal is applied thereto; and a determination circuit configured to receive a first electrical signal and a second electrical signal and to determine the moisture in the soil based on the first resonant frequency of the first electrical signal and the second resonant frequency of the second electrical signal.

13 Claims, 7 Drawing Sheets

(56) References Cited

U.S. PATENT DOCUMENTS

| | | |
|---|---|---|
| 5,621,669 A | 4/1997 | Bjornsson |
| 9,077,183 B2 | 7/2015 | Thomas et al. |
| 9,658,178 B2 | 5/2017 | Surman et al. |
| 2008/0199359 A1 | 8/2008 | Davis et al. |
| 2009/0219037 A1* | 9/2009 | Campbell ............ G01N 33/246 |
| | | 324/664 |
| 2015/0330932 A1 | 11/2015 | Kumaran et al. |
| 2017/0239540 A1 | 8/2017 | Chan et al. |
| 2017/0241923 A1 | 8/2017 | Chan et al. |
| 2017/0241973 A1 | 8/2017 | Chan et al. |
| 2017/0363551 A9 | 12/2017 | Chan et al. |

FOREIGN PATENT DOCUMENTS

| | | |
|---|---|---|
| JP | 2013-200194 A | 10/2013 |
| JP | 2016-217795 A | 12/2016 |
| KR | 10-2016-0109121 A | 9/2016 |
| KR | 101767338 B1 | 8/2017 |
| WO | 2017-021950 A2 | 2/2017 |

\* cited by examiner

SOIL MOISTURE SENSOR AND OPERATING METHOD THEREOF

CROSS-REFERENCE TO RELATED APPLICATIONS

This application is a continuation of PCT/KR2019/014124 filed on Oct. 25, 2019, which claims priority to Korean Patent Application Nos. 10-2018-0128105 and 10-2019-0119988 filed on Oct. 25, 2018 and Sep. 27, 2019, respectively, which applications are incorporated herein by reference in their entireties.

TECHNICAL FIELD

The present invention relates generally to a soil moisture sensor for measuring the moisture content of the soil and an operating method thereof, and more particularly to a soil moisture sensor for measuring the moisture content of the soil by detecting a change in the frequency formed in a sensing circuit according to the moisture content in the soil and an operating method thereof.

BACKGROUND ART

Conventional methods for measuring the moisture of the soil include a dry basis weight method, a tactile method that evaluates the moisture of the soil based on the texture of each soil, a method of measuring the electrical conductivity of moisture absorbed in the capillary pores of a gypsum block, an unglazed porous cup moisture tensiometer method, and a neutron probe method.

Although a method of determining the weight percentage of moisture using the dry basis weight method has been a representative method of measuring moisture for a long period of time, the procedure thereof is cumbersome and time-consuming, thereby causing inconvenience. The tactile method that evaluates the moisture of the soil based on the texture of each soil is inefficient in that the individual variation of each evaluator is large and considerable training is required. The method of measuring the electrical conductivity of moisture absorbed in the capillary pores of a gypsum block in a relatively simple way has a disadvantage in that the pores of the gypsum block are very fine, so that when the soil moisture tension is low, almost all of the pores are saturated, resulting in unsatisfactory results. Although the unglazed porous cup moisture tensiometer method is also widely adopted for determining an irrigation point, it has a disadvantage in that it does not work in a region where the moisture tension is higher than 1 atmosphere.

The neutron probe method has a disadvantage in that it is not widely used for general purposes because the initial calibration procedure thereof is difficult, the transport, measurement and operation thereof are cumbersome, and the price thereof is considerably high.

Furthermore, there was proposed a time domain reflectometry (TDR) method using the principle in which only the dielectric properties of water according to the rotational motion of water molecules stood out because the movement of ions in the gigahertz field was negligibly reduced. The TDR method is a method of emitting a gigahertz-level high energy frequency to a sensor using an uncovered iron rod inserted into the soil as a condenser and analyzing a time difference or voltage difference according to the number of frequencies reflected according to the degree of permittivity based on the moisture of the soil. The TDR method quantifies the moisture of the soil by simply amplifying reflected electromagnetic waves transformed by a soil condenser using the principle in which electromagnetic waves are transformed by a condenser and reading them using an oscilloscope. Accordingly, disadvantages have been raised in that the necessary equipment is relatively complex and expensive.

For this reason, there is urgently required the development and introduction of an inexpensive soil moisture measurement device that is simpler, has a simpler operation and procedure, and can measure and collect accurate data within a short period of time.

Meanwhile, Japanese Patent Application Publication No. 2016-217795 entitled "Moisture Sensor and Moisture Measuring Device" discloses a moisture sensor in which a resonance circuit whose resonant frequency changes in response to a change in the equivalent inductance attributable to a change in the moisture content contained in the soil is formed using a moisture sensor having electrodes composed of comb teeth intersecting each other and the resonant frequency generated by the resonance circuit is calculated.

However, even according to the related art, a problem arises in that it is difficult to measure a resonant frequency rapidly and accurately because the process of calculating a resonant frequency by converting a measured amplitude value rather than directly measuring a resonant frequency is complicated. For this reason, a problem arises in that when the moisture content of the soil is measured in real time, noise is generated and thus a measured value is inaccurate.

SUMMARY

The related art is configured to scan the magnitude of an output electrical signal formed in a resonance circuit in response to an input electrical signal by varying the frequency of the input electrical signal applied to the resonance circuit and calculate a frequency in the case of having a maximum size as a resonant frequency. For this reason, the related art is problematic in that it has an error corresponding to the resolution of the variable frequency of the input electrical signal, accuracy is degraded by an indirect method of calculating the resonant frequency by detecting the magnitude of the electrical signal, and a relatively long time is required because the frequency of the input electrical signal needs to be varied.

The present invention was conceived to overcome the above-described problems of the related art, and an object of the present invention is to provide a soil moisture sensor that generates high-frequency signals in a circuit having a capacitance formed in a probe for a soil moisture sensor using the soil as a medium and in a circuit having a reference capacitance, respectively, measures and compares frequencies for the high-frequency signals in the two circuits, and quantifies moisture content in the soil, thereby enabling the moisture state of the soil to be more accurately determined in real time.

Furthermore, an object of the present invention is to provide a soil moisture sensor that is non-destructive and semi-permanently usable, provides the stability of the device, and may significantly reduce manufacturing cost compared to the conventional soil moisture sensor because it does not require a configuration for varying the frequency of an input electrical signal.

An object of the present invention is to provide a soil moisture sensor that proposes a circuit and an operating method capable of effectively detecting the shift of a resonant frequency. Furthermore, an object of the present invention is to provide a soil moisture sensor that may shorten soil moisture detection time because it does not require the process of varying the frequency of an input electrical signal.

An object of the present invention is to provide a soil moisture sensor that may further include a temperature sensor in order to more accurately detect the moisture content of the soil and may measure precise moisture content by compensating the moisture content of the soil based on the temperature sensor.

According to an aspect of the present invention, there is provided a soil moisture sensor including: a first probe including a pair of first electrodes extending in a first direction in order to penetrate into the soil; a first resonance circuit connected to the pair of first electrodes of the first probe through a pair of first ports, and configured such that a first alternating current (AC) signal is applied thereto; a second resonance circuit having the same impedance as the first resonance circuit, and configured such that a second AC signal having the same characteristics as the first AC signal while being a reference AC signal is applied thereto; and a determination circuit configured to receive a first electrical signal formed in the first resonance circuit, to receive a second electrical signal formed in the second resonance circuit, and to determine the moisture in the soil based on the first resonant frequency of the first electrical signal and the second resonant frequency of the second electrical signal.

The soil moisture sensor according to an embodiment of the present invention may further include a temperature sensor coupled to any one of the pair of first electrodes of the first probe.

The determination circuit may be further configured to generate a first determination value for the moisture in the soil based on the first resonant frequency of the first electrical signal and the second resonant frequency of the second electrical signal, and may also be configured to generate a second determination value for the moisture in the soil by compensating the first determination value based on a temperature measured by the temperature sensor.

The determination circuit may be further configured to detect a quantitative change in the first resonant frequency of the first electrical signal formed in the first resonance circuit based on a capacitance formed between the pair of first electrodes by the moisture contained in the soil located between the pair of first electrodes, and may also be configured to determine the moisture contained in the soil based on the detected quantitative change in the first resonant frequency. In this case, the determination circuit may be further configured to generate a first determination value for the moisture contained in the soil based on the detected quantitative change in the first resonant frequency, and may also be configured to generate a second determination value by compensating the first determination value based on the measured temperature.

The determination circuit may be further configured to detect the difference between the second resonant frequency, which is a reference resonant frequency of the second electrical signal formed in the second resonance circuit under the influence of the second AC signal applied to the second resonance circuit, and the first resonant frequency, and may also be configured to determine the moisture contained in the soil based on the difference between the second resonant frequency and the first resonant frequency. In this case, the determination circuit may be further configured to generate a first determination value for the moisture contained in the soil based on the difference between the second resonant frequency and the first resonant frequency, and may also be configured to generate a second determination value by compensating the first determination value based on the measured temperature.

The determination circuit may be further configured to, if the difference between the second resonant frequency and the first resonant frequency is equal to or larger than a first threshold value, consider that the first resonant frequency has caused a significant change and determine the presence of the moisture contained in the soil.

The determination circuit may include: an operator circuit configured to obtain the difference between the first resonant frequency and the second resonant frequency; a low-pass filter connected to the output terminal of the operator circuit, and configured to remove a high-frequency component; and a time-to-digital converter connected to the output terminal of the low-pass filter, and configured to digitally count the frequency of a third frequency component signal corresponding to the difference between the first resonant frequency and the second resonant frequency.

The soil moisture sensor may further include a second probe including a pair of second electrodes formed to come into contact with or penetrate into the surface layer of the soil, and the second resonance circuit may be connected to the pair of second electrodes included in the second probe via a pair of second ports.

The determination circuit may be further configured to determine the moisture contained in the soil based on the quantitative difference between the second resonant frequency of the second electrical signal, formed in the second resonance circuit based on a second capacitance formed between the pair of second electrodes, and the first resonant frequency.

According to another aspect of the present invention, there is provided a soil moisture sensing method, including: applying, by a first oscillator, a first alternating current (AC) signal via a first resonance circuit that is connected to a pair of first electrodes of a first probe including the pair of first electrodes extending in a first direction in order to penetrate into the soil through a pair of first ports; applying, by a second oscillator having the same characteristics as the first oscillator, a second AC signal, which is a reference AC signal, to a second resonance circuit having the same impedance as the first resonance circuit; receiving, by a determination circuit, a first electrical signal formed in the first probe and the first resonance circuit under the influence of the first AC signal; receiving, by the determination circuit, a second electrical signal formed in the second resonance circuit under the influence of the second AC signal applied to the second resonance circuit; and determining, by the determination circuit, the moisture contained in the soil located between the pair of first electrodes of the first probe based on the first resonant frequency of the first electrical signal and the second resonant frequency of the second electrical signal.

In this case, the soil moisture sensing method according to an embodiment of the present invention may further include measuring, by a temperature sensor coupled to any one of the pair of first electrodes of the first probe, the temperature of the soil. In this case, the determination circuit may generate a first determination value for the moisture in the soil based on the first resonant frequency of the first electrical signal and the second resonant frequency of the second electrical signal, and may generate a second determination value for the moisture contained in the soil by compensating the first determination value based on a measured temperature of the soil.

The generating may include: detecting a quantitative change in the first resonant frequency of the first electrical signal formed in the first resonance circuit based on the capacitance formed between the pair of first electrodes by the moisture contained in the soil located between the pair of first electrodes; and determining the moisture contained in the soil based on the detected quantitative change in the first resonant frequency.

The soil moisture sensing method may further include detecting, by the determination circuit, the difference between the first resonant frequency and the second resonant frequency, and the generating may include determining the moisture contained in the soil located between the pair of first electrodes of the first probe based on the difference between the first resonant frequency and the second resonant frequency.

The soil moisture sensing method may further include applying, by the second oscillator, the second AC signal to a second probe, connected to the second resonance circuit through a pair of second ports and including a pair of second electrodes formed to come into contact with or penetrate into a surface layer of the soil, via the pair of second ports.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Other objects and features of the present invention in addition to the above-described objects will be apparent from the following description of embodiments with reference to the accompanying drawings. Embodiments of the present invention will be described in detail below with reference to the accompanying drawings. In the following description, when it is determined that a detailed description of a related known component or function may unnecessarily make the gist of the present invention obscure, it will be omitted. Soil moisture sensors and operating methods thereof according to embodiments of the present invention will be described in detail below with reference to FIGS. 1 to 6.

Figure 1:
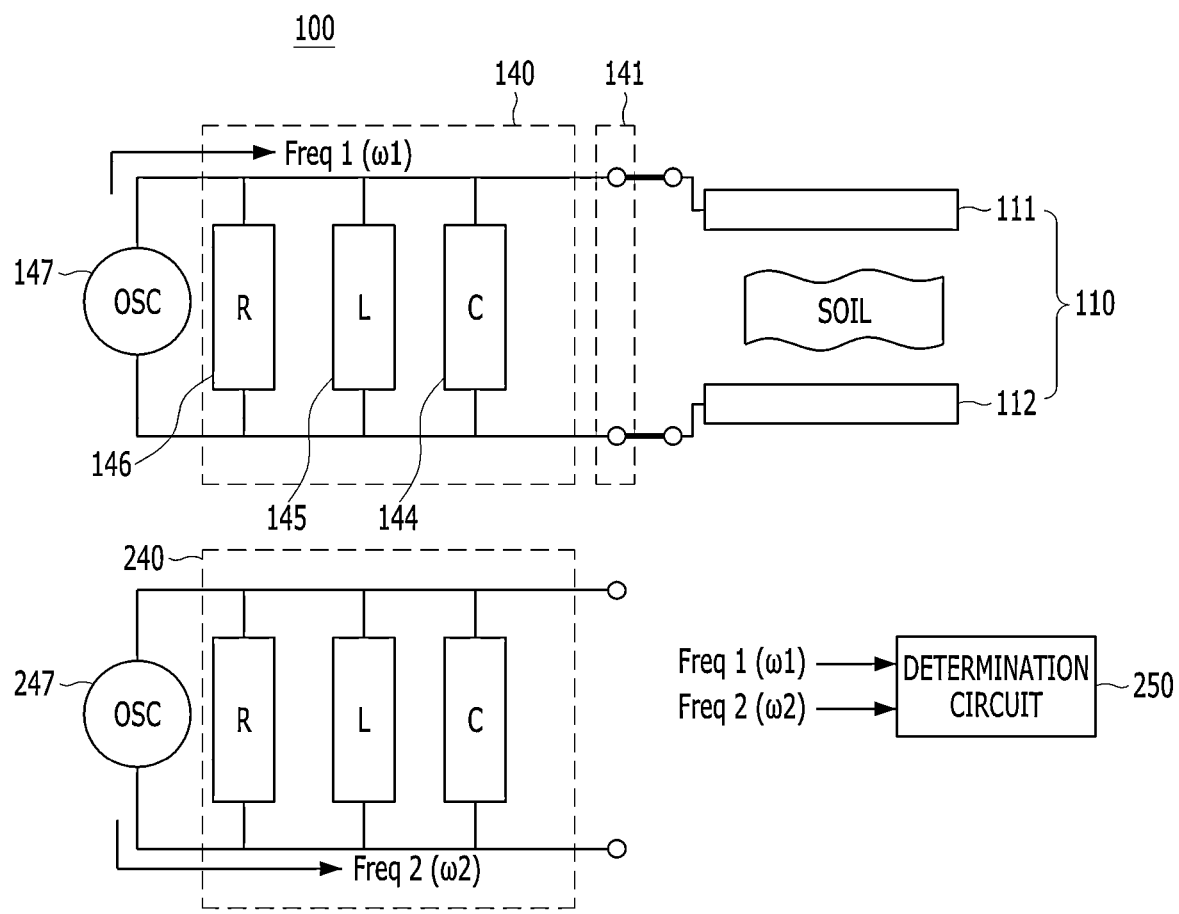
FIG. 1 is a diagram showing a soil moisture sensor according to an embodiment of the present invention.

FIG. 1 is a diagram showing a soil moisture sensor 100 according to an embodiment of the present invention.

Referring to FIG. 1, the soil moisture sensor 100 according to the present embodiment includes a first probe 110, a first resonance circuit 140, first ports 141, a first oscillator 147, a second resonance circuit 240, a second oscillator 247, and a determination circuit 250.

The first probe 110 includes a pair of first electrodes 111 and 112 including an electrode 111 and an electrode 112 disposed to face the electrode 111 in parallel with the electrode 111. The pair of first electrodes 111 and 112 of the first probe 110 may be formed to extend in a direction toward the soil in order to penetrate into the soil.

The first resonance circuit 140 is connected to the pair of first electrodes 111 and 112 of the first probe 110 via the pair of ports 141, and applies a first AC signal to the first probe 110. Furthermore, the first resonance circuit 140 includes a first inductor 145 and a first capacitor 144. Although the first inductor 145 may have the form of a coil, it may be implemented in the form of a semiconductor pattern having a controllable inductance. Referring to FIG. 1, a first parasitic resistor 146 formed in the first resonance circuit 140 is illustrated. According to an embodiment of the present invention, a resistor R' (not shown) may be additionally disposed for the purpose of balancing between the first resonance circuit 140 and other circuits to be described later.

The first oscillator 147 applies a first AC signal to the first resonance circuit 140. The first resonant frequency $\omega 1$ of a first electrical signal formed in the first resonance circuit 140 by the application of the first AC signal may be determined based on a capacitance formed by the moisture contained in the soil located between the impedance of the first resonance circuit 140 and the pair of first electrodes 111 and 112 of the first probe 110.

Furthermore, the first oscillator 147 may apply the first AC signal to the pair of first electrodes 111 and 112 of the first probe 110 via the first ports 141. The applied first AC signal is applied to the combined impedance of the capacitance formed by the moisture contained in the soil located between the first resonance circuit 140 and the pair of first electrodes 111 and 112 of the first probe 110, and thus the first electrical signal is formed in the first resonance circuit 140 and the first probe 110. In this case, the ports 141 function as interface ports between the first resonance circuit 140 and the pair of first electrodes 111 and 112 of the first probe 110.

Meanwhile, the soil moisture sensor 100 of the present invention may be implemented by forming the first resonance circuit 140, the first oscillator 147, the second resonance circuit 240, the second oscillator 247, and the determination circuit 250 as an integrated circuit (IC). In this case, the integrated circuit may be connected with the pair of first electrodes 111 and 112 of the first probe 110 via the first ports 141 functioning as interface ports.

When the determination circuit 250 of the soil moisture sensor is fabricated as a single chip as described above, the sensor circuit and the reference resonance circuit are disposed close to each other and composed of the same type of devices in the same semiconductor wafer. Accordingly, the measurement error attributable to semiconductor process variation may be reduced, and thus the moisture content in the soil may be accurately determined in real time.

The first resonant frequency $\omega 1$ of the first electrical signal may be determined based on the moisture contained in the soil located between the pair of first electrodes 111 and 112 of the first probe 110.

In other words, due to a change in the capacitance formed by the moisture contained in the soil located between the pair of first electrodes 111 and 112 of the first probe 110, the impedance of the first resonance circuit 140 and the capacitance formed in the first probe 110 are connected in parallel to each other, and thus a change in a combined impedance having an arithmetically summed capacitance may be determined. The first AC signal is applied to the impedance to form a first electrical signal having a first resonant frequency $\omega1$ in the first resonance circuit 140. Likewise, a first electrical signal having a first resonant frequency $\omega1$ is formed in the first probe 110 including the pair of first electrodes 111 and 112.

The second resonance circuit 240 is designed to have the same impedance as the first resonance circuit 140. In particular, an inductor L and a capacitor C in the second resonance circuit 240 may be designed to have the same values as the first inductor 145 and the first capacitor 144 in the first resonance circuit 140. Furthermore, the second resonance circuit 240 may be disposed close to the first resonance circuit 140 in the semiconductor wafer so that they can be less affected by semiconductor process variation during the fabrication of the semiconductor.

Meanwhile, although the parasitic resistance component R in the second resonance circuit 240 is illustrated, a resistor R' (not shown) may be additionally included in order to allow the impedances of the first and second resonance circuits 140 and 240 to accurately match each other and improve balancing according to an embodiment of the present invention.

A second AC signal applied by the second oscillator 247 is applied to the second resonance circuit 240. The applied second AC signal is applied to the impedance of the second resonance circuit 240 to form a second electrical signal in the second resonance circuit 240. The second AC signal is a reference AC signal, and thus the second electrical signal formed in the second resonance circuit 240 is a reference electrical signal. In this case, the second electrical signal has a second resonant frequency $\omega2$, which is a reference resonant frequency.

Since the second resonance circuit 240 is not exposed to the outside, the electrical characteristics of the second resonance circuit 240 are not affected regardless of the presence or absence of the moisture contained in the soil. Accordingly, the second electrical signal may maintain the second resonant frequency $\omega2$, which is a reference resonant frequency, regardless of the presence or absence of the moisture contained in the soil.

The first electrical signal having the first resonant frequency $\omega1$ formed in the first resonance circuit 140 and the second electrical signal having the second resonant frequency $\omega2$ formed in the second resonance circuit 240 are transmitted to the determination circuit 250. The operations of the second oscillator 247 and the second resonance circuit 240 may also be controlled by a control unit/controller/processor (not shown) included in the determination circuit 250.

The determination circuit 250 may receive the first electrical signal having the first resonant frequency $\omega1$ formed in the first resonance circuit 140, may receive the second electrical signal having the second resonant frequency $\omega2$ formed in the second resonance circuit 240, and may determine the moisture content contained in the soil located between the pair of first electrodes 111 and 112 of the first probe 110 based on the first resonant frequency $\omega1$ and the second resonant frequency $\omega2$.

In this case, the determination circuit 250 may determine the moisture content contained in the soil located between the pair of first electrodes 111 and 112 of the first probe 110 through the value of a change in the first resonant frequency $\omega1$.

The determination circuit 250 may detect a quantitative change in the first resonant frequency $\omega1$ of the first electrical signal formed in the first resonance circuit 140 based on the capacitance formed according to the moisture content contained in the soil located between the pair of first electrodes 111 and 112 of the first probe 110, and may measure the moisture content contained in the soil located between the pair of first electrodes 111 and 112 of the first probe 110 based on the detected quantitative change in the first resonant frequency $\omega1$.

More specifically, the capacitance may be represented by the equation below:

$$C = \varepsilon \cdot \frac{S}{d} = \varepsilon_r \cdot \varepsilon_0 \cdot \frac{S}{d} \tag{1}$$

where C is the capacitance, $\varepsilon$ is a permittivity constant, S is the area of opposite electrodes, and d is the distance between the electrodes.

The permittivity constant $\varepsilon$ and the capacitance C are proportional to each other. Furthermore, $\varepsilon_0 = 8.854 \ast 10-12$ F/m (the permittivity of vacuum), and $\varepsilon$=Relative Permittivity The permittivity constant $\varepsilon$ uses the relative permittivity $\varepsilon_r$, which is a ratio with respect to the permittivity $\varepsilon_0$ of specific vacuum, as a characteristic value.

Since the relative permittivity of air is similar to that of vacuum and the relative permittivity $\varepsilon_r$ of water is about 80 and relatively much larger than that of air and soil particles, the permittivity constant of soil is significantly affected by the moisture content of the soil. Since the voids in the soil are also similar to the air, they do not significantly affect a change in the relative permittivity attributable to the moisture content. Meanwhile, the relative permittivity of vacuum is always maintained at 1 regardless of a change in temperature, but the permittivity of water decreases as the temperature increases. Therefore, as the moisture content contained in the soil increases at a constant temperature, the permittivity constant of the soil will increase, and thus the capacitance of the soil will increase.

The resonant frequency f of a circuit for detecting the moisture contained in the soil and a reference circuit may be represented by the equation below:

$$f = \frac{1}{2\pi \cdot \sqrt{L \cdot C}} \tag{2}$$

where L is inductance and C is capacitance. The resonant frequency f and the capacitance C are inversely proportional to each other. Therefore, as the capacitance of the soil increases, the resonant frequency f decreases.

In the circuit for detecting the moisture contained in the soil, as the moisture content contained in the soil located between the pair of first electrodes 111 and 112 of the first probe 110 increases, the capacitance that is coupled to the first probe 110 increases. Accordingly, the first resonant frequency $\omega1$ of the first electrical signal formed by the combined capacitance of the first resonance circuit 140 that is connected in parallel and added arithmetically will decrease.

The pair of first electrodes 111 and 112 of the first probe 110 configured to measure the moisture content of the soil are connected only to the first resonance circuit 140 via the first ports 141, but are not connected to the second resonance circuit 240 of the reference resonance circuit. The first resonant frequency ω1 of the first electrical signal may be determined based on the moisture contained in the soil located between the pair of first electrodes 111 and 112 of the first probe 110. More specifically, as the combined impedance, in which the impedance and capacitance of the first resonance circuit 140 are connected in parallel to each other and added arithmetically, changes due to a change in the capacitance formed according to the moisture content contained in the soil located between the pair of first electrodes 111 and 112 of the first probe 110, the first resonant frequency ω1 of the first electrical signal also changes.

Meanwhile, unlike the first resonance circuit 140, the second resonance circuit 240 is not connected to the first probe 110 configured to measure the moisture content of the soil, and thus the second resonance circuit 240 maintains the second resonant frequency ω2 regardless of the presence or absence of the moisture in the soil. In this case, the second resonance circuit 240 may generate the second electrical signal having the second resonant frequency ω2 based on the capacitance using air as a medium.

Therefore, when the difference in frequency between the second electrical signal of the second resonance circuit 240 and the first electrical signal of the first resonance circuit 140 is detected, it may be determined whether the first resonant frequency ω1 of the first resonance circuit 140 has been shifted from the resonant frequency ω2, and also the degree of shift may be quantitatively analyzed if it has been shifted.

The reference resonance circuit may track a change in the first resonant frequency ω1 generated in the first resonance circuit 140, may remove the noise added to the first resonant frequency ω1 measured by the determination circuit 250 in real time, and may accurately measure the degree of change in the first resonant frequency ω1.

When the first probe 110 is inserted into the soil, the first resonant frequency ω1 changes due to the influence of the capacitance formed between the first electrodes 111 and 112 via the soil. In this case, in the considerably dry soil such as dry sand or dry wasteland, a change in the first resonant frequency ω1 is not large. In contrast, in the case of the soil containing moisture, a relatively large change in the first resonant frequency ω1 is detected.

The determination circuit 250 may detect the difference between the second resonant frequency ω2, which is the reference resonant frequency of the second electrical signal formed in the second resonance circuit 240 under the influence of the second AC signal applied to the second resonance circuit 240, and the first resonant frequency ω1, and may determine the moisture content contained in the soil from the first probe 110 based on the difference (ω2−ω1) between the second resonant frequency and the first resonant frequency.

Meanwhile, when a foreign material such as a conductor enters the soil in the first probes 110, or when the soil contains a large amount of moisture, e.g., when the soil becomes muddy, the electrical characteristic between the pair of first electrodes 111 and 112 of the first probe 110 may significantly deviate from an initially assumed range. In addition, when the moisture content contained in the soil is excessive, e.g., even when water flows out of the soil or when the soil is submerged in water (which is not the ordinary case of soil moisture detection), the capacitance coupled to the first probe 110 may significantly deviate from the initially assumed range (e.g., the difference (ω2−ω1) is positive). In this case, according to an embodiment of the present invention, the first resonant frequency ω1 may have a higher value than the second resonant frequency ω2, and thus the difference between the second resonant frequency ω2 and the first resonant frequency ω1 may have a negative value.

In this case, the determination circuit 250 may determine that detection is inappropriate (not in the ordinary case), and may notify the user of an error through a visual or aural means such as a display or a speaker.

Meanwhile, the determination circuit 120 may have a plurality of reference values for the resonant frequency according to a quantitative change in the first resonant frequency ω1. When the difference between the first resonant frequency ω1 and the second resonant frequency ω2 is defined as a first threshold value in the case where the moisture content of the soil is not measured, i.e., in the case where there is no soil located between the pair of first electrodes 111 and 112 of the first probe 110, the determination circuit 250 may consider that a significant change has occurred in the first resonant frequency ω1 if the change value of the first resonant frequency ω1 is equal to or higher than a first threshold value, and may thus determine that the moisture content contained in the soil has a significant value.

The second electrical signal having the second resonant frequency ω2, which is the reference resonant frequency formed from the second AC signal applied from the second oscillator 247 having the same frequency or phase as the first oscillator 147 is formed in the second resonance circuit 240 that is disposed close to the first resonance circuit 140 and includes the capacitor C configured to have the same capacitance as the first capacitor 144 in order to have the same impedance, the inductor L configured to have the same inductance as the first inductor 145, and the resistor R configured to have the same resistance value as the first parasitic resistor 146. There may be a specific difference in frequency between the second electrical signal having the second resonant frequency ω2 and the first electrical signal having the first resonant frequency ω1.

The determination circuit 250 may set the specific difference in frequency as an offset, may define it as a first threshold value, and may thus consider that a significant change has occurred in the first resonant frequency ω1 only when the difference between the second resonant frequency ω2 and the first resonant frequency ω1 is equal to or higher than the first threshold value and then determine that the moisture content contained in the soil has a significant value.

Alternatively, according to an embodiment of the present invention, the determination circuit 250 may define changes in the first resonant frequency ω1 as a second threshold value, a third threshold value, and a fourth threshold value according to multiples of the first threshold value, and may classify and determine the levels of the moisture contents contained in the soil.

The determination circuit 250 may further include a control unit/controller/processor (not shown) configured to control the operations of the first oscillator 120 and the first resonance circuit 140 therein. A first AC signal is applied from the first oscillator 120 to the first resonance circuit 140 in response to a control command from the control unit, and the determination circuit 250 may receive information about the first resonant frequency ω1 of the first electrical signal formed in the first resonance circuit 140.

Furthermore, the determination circuit 250 may perform a calibration process. The determination circuit 250 may perform a calibration process when the determination circuit 250 does not measure the moisture content of the soil, i.e., when there is no moisture contained in the soil located between the pair of first electrodes 111 and 112 of the first probe 110. In this case, the first resonance circuit 140 or the second resonance circuit 240 may be adjusted such that the difference between the first resonant frequency ω1 and the second resonant frequency ω2 becomes zero through the calibration process.

The difference between the first resonant frequency ω1, detected in the absence of the moisture contained in the soil located between the pair of first electrodes 111 and 112 of the first probe 110 through the calibration process, and the second resonant frequency ω2 may be stored in separate memory or storage, and may be used as offset information in a future soil moisture detection process.

After the calibration, the adjustment of the difference between the first resonant frequency ω1 and the second resonant frequency ω2 may be performed using a means such as the adjustment of the value of the variable resistor R'.

Figure 2:
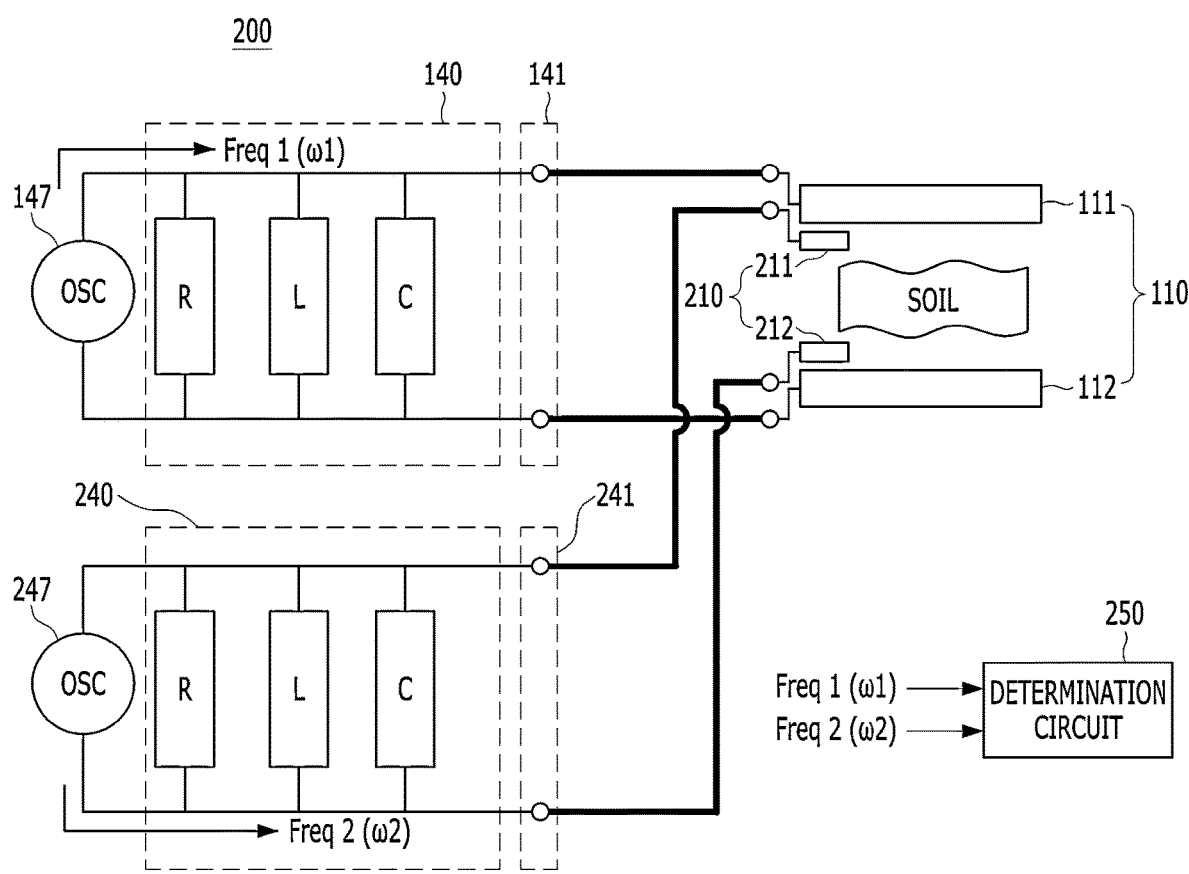
FIG. 2 is a diagram showing a soil moisture sensor according to an embodiment of the present invention.

FIG. 2 is a diagram showing a soil moisture sensor 200 according to an embodiment of the present invention. Referring to FIG. 2, the soil moisture sensor 200 includes a first probe 110, a first resonance circuit 140, first ports 141, a first oscillator 147, a second probe 210, a second resonance circuit 240, second ports 241, a second oscillator 247, and a determination circuit 250.

Since the first resonance circuit 140, first ports 141, first oscillator 147, second resonance circuit 240, second ports 241, second oscillator 247, and first probe 110 of FIG. 2 have been sufficiently described based on the items shown in FIG. 1, redundant descriptions thereof will be omitted. The descriptions of the operation of the determination circuit 250 of FIG. 2 that is very similar to those of the operation of the determination circuit 250 of FIG. 1 will be omitted.

Referring to FIG. 2, the second resonance circuit 240 is connected to the pair of second electrodes 211 and 212 of the second probe 210 via the second ports 241. The second probe 210 will be described in detail with reference to FIG. 3.

Figure 3:
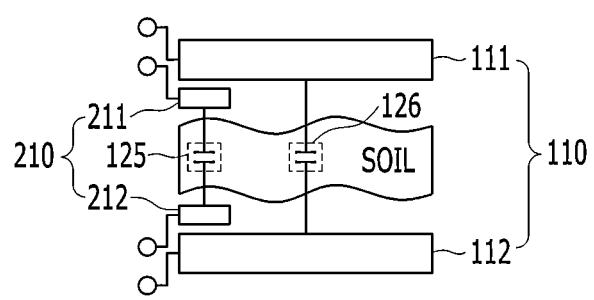
FIG. 3 is a diagram illustrating the operating principle of a first probe and a second probe.

FIG. 3 is a diagram illustrating the operating principle of the first probe 110 and the second probe 210. Referring to FIG. 3, the first probe 110 may measure the moisture content contained in the soil located between the pair of first electrodes 111 and 112 that deeply penetrate into the soil, as described above. The second probe 210 is disposed in parallel with the first probe 110, and includes a pair of second electrodes 211 and 212 extending in a direction in which they penetrate into the soil.

The second probe 210 is electrically connected to the second resonance circuit 240, which is a reference resonance circuit, and the second oscillator 247 via the second ports 241. This may be intended for the purpose of removing an offset attributable to the moisture content or temperature of the soil measured by the first probe 110. Accordingly, the length of the second probe 210 may be shorter than that of the first probe 110 so that the second probe 210 may penetrate into only the surface layer of the soil in order to measure the capacitance value of the soil itself where there is no significant difference from the temperature in a measurement state and there is little moisture contained in the soil.

The second probe 210 is shorter than the first probe 110 in order to penetrate into only the surface layer of the soil or come into contact with the surface layer of the soil, and is disposed close to the first probe 110 in parallel with the first probe 110. The first probe 110 may measure a capacitance value 126 attributable to the moisture contained in the soil in a deep layer or inner part of the soil. The second probe 210 may measure a capacitance value 125 attributable to the moisture contained in the soil in the surface layer of the soil.

The evaporation of moisture is little in the deep or inner part of the soil, and thus it may be possible to accurately measure the capacitance value 126 attributable to the moisture contained in the soil. The evaporation of moisture is much in the surface part of the soil, and thus it may possible to measure the capacitance value 125 for the soil itself (the soil excluding moisture) that does not contain moisture therein.

The determination circuit 250 may determine whether the moisture content contained in the soil located between the pair of first electrodes 111 and 112 of the first probe 110 has a significant value by taking into consideration the capacitance value 126 attributable to the moisture contained in the soil substantially in the deep or inner part of the soil and the capacitance value 125 for the soil itself without moisture contained in the soil substantially in the surface part of the soil through a calibration process.

In this case, the determination circuit 250 may detect the moisture content in the soil based on the difference between the first resonant frequency ω1 generated by the capacitance value 126 attributable to the moisture contained in the soil substantially in the deep or inner part of the soil and the second resonant frequency ω2 generated by the capacitance value 125 for the soil without moisture contained in the soil substantially in the surface part of the soil as a minimum threshold value.

Figure 4:
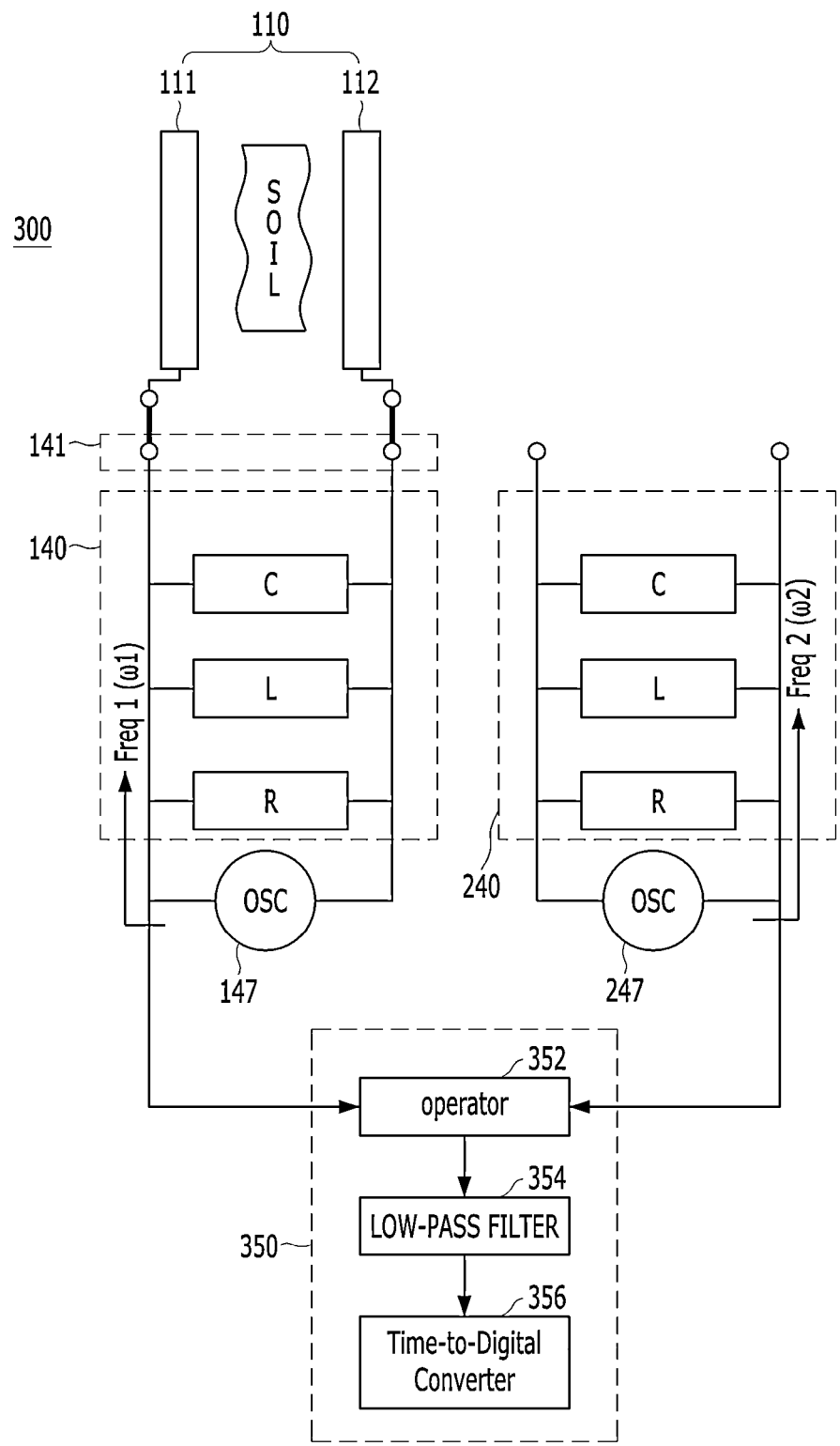
FIG. 4 is a diagram showing a soil moisture sensor according to an embodiment of the present invention.

FIG. 4 is a diagram showing a soil moisture sensor 300 according to an embodiment of the present invention. The soil moisture sensor 300 according to the present embodiment of the present invention includes a first probe 110, a first resonance circuit 140, first ports 141, a first oscillator 147, a second resonance circuit 240, second ports 241, a second oscillator 247, and a determination circuit 350.

Since the first probe 110, first resonance circuit 140, first ports 141, second resonance circuit 240, second ports 241, first oscillator 147, and second oscillator 247 of FIG. 4 have been sufficiently described based on the items shown in FIGS. 1 to 3, redundant descriptions thereof will be omitted. The descriptions of the operation of the determination circuit 350 of FIG. 4 that is very similar to those of the operation of the determination circuit 250 of FIGS. 1 to 3 will be omitted.

In FIG. 4, the determination circuit 350 includes an operator circuit 352, a low-pass filter 354, and a time-to-digital converter 356.

The operator circuit 352 obtains the difference between the first resonant frequency ω1 and the second resonant frequency ω2. As an example of the simplest method for obtaining the difference between the first resonant frequency ω1 and the second resonant frequency ω2, there may be a method in which the operator circuit 352 multiplies the first resonant frequency ω1 and the second resonant frequency ω2. The low-pass filter 354 is connected to the output terminal of the operator circuit 352, and removes high-frequency components. Accordingly, the low-frequency signal of a third frequency component corresponding to the difference between the first resonant frequency ω1 and the second resonant frequency ω2 is generated.

The time-to-digital converter 356 is connected to the output terminal of the low-pass filter 354, and digitally counts the frequency of the third frequency component signal. In this case, the time-to-digital converter 356 may output a digitized value proportional to the frequency of the third frequency component signal.

According to an embodiment, the time-to-digital converter 356 may generate a pulse signal having a fourth frequency proportional to the frequency of the third frequency component signal. Although the fourth frequency may be the same as the frequency of the third frequency component signal, the fourth frequency may become a frequency different from a first frequency due to the influence of a transfer function reflected via the operator circuit 352 and the low-pass filter 354. The time-to-digital converter 356 may count the number of pulses of the pulse signal having the fourth frequency for a predetermined period of time, or may generate a digital count value for the pulse width or period of the pulse signal having the fourth frequency.

The digitized count value generated by the determination circuit 350, i.e., a digitized value proportional to the frequency of the third frequency component signal, may be converted into an analog signal proportional to the digitized value again according to the configuration of the soil moisture sensor 300, and may be transmitted to the main processor side of the soil moisture sensor 300. In this case, the voltage, current, frequency, or amplitude of the analog signal may be converted into a value proportional to the frequency of the third frequency component signal.

The first threshold value and the second threshold value applied in the determination circuit 250 of the previous embodiment may be applied to digital count values generated as the output of the time-to-digital converter 356. According to an embodiment of the determination circuit 350, a sampler and comparator for the third frequency component signal may be included. In this case, for the smooth operation of the determination circuit 350, the sampler and the comparator may be designed by selecting an operating frequency sufficiently higher than the frequency component corresponding to the second threshold value.

The time it takes for the soil moisture sensor 300 to determine the moisture contained in the soil is about hundreds of milliseconds to a few seconds. The process of determining the moisture content of the soil according to the present invention may detect a complete result within hundreds of microseconds to a few milliseconds. As described above, since the soil moisture sensor 300 according to the present invention uses the time-to-digital converter instead of a PLL loop, the stable operation of the circuit is possible without a control loop, the manufacturing cost is low, and the implementation of the constituent circuits is simple.

The determination circuit 350 of the present invention may generate a determination result, obtained by applying the first threshold value and the second threshold value to the digital count value, as a separate signal, and may transmit it to the main processor of the soil moisture sensor 300.

The main processor may detect that the moisture content contained in the soil has a significant value in the case of the first threshold value, and may determine that the moisture content contained in the soil has a larger value in the case of the second threshold value. In addition, the level of the moisture content contained in the soil may be determined based on a plurality of threshold values set as a plurality of set reference values. In an embodiment of the present invention, the second threshold may be larger than the first threshold.

Meanwhile, the determination circuits 250 of the soil moisture sensors 100 and 200 shown in FIGS. 1 to 2 may be designed to operate in the same manner as the determination circuit 350 of the soil moisture sensor 300 shown in FIG. 4. In addition, the soil moisture sensors 100, 200, and 300 of the present invention may be implemented by forming the first resonance circuit 140, the first oscillator 147, the second resonance circuit 240, the second oscillator 247, and the determination circuit 250 or 350 as one integrated circuit (IC). In this case, the integrated circuit may be connected to the pair of first electrodes 111 and 112 of the first probe 110 and the pair of second electrodes 211 and 212 of the second probe 210 through the first ports 141 and the second ports 241 functioning as interface ports.

Figure 5:
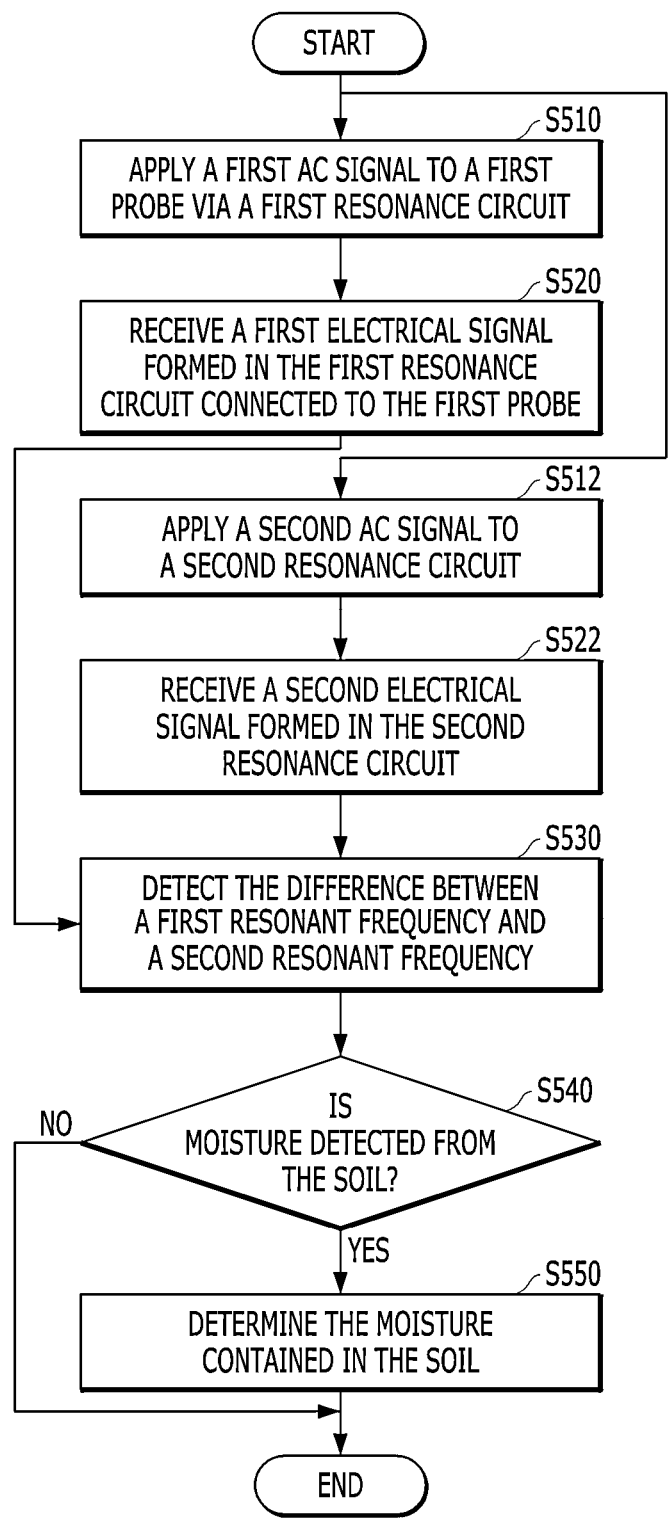
FIG. 5 is an operational flowchart showing a method of determining moisture contained in the soil according to an embodiment of the present invention.

FIG. 5 is an operational flowchart showing a method of determining moisture contained in the soil according to an embodiment of the present invention. The soil moisture sensing method of the present invention may be performed by the soil moisture sensor 100 of FIG. 1 or a control unit (not shown) therein.

Referring to FIG. 5, a first AC signal is applied to the pair of first electrodes 111 and 112 of the first probe 110 and the first resonance circuit 140 by the first oscillator 147 at step S510. The operation of the first oscillator 147 or the operation of applying the first AC signal may be controlled by a control unit/controller/processor (not shown).

Due to the application of the first AC signal, a first electrical signal is formed in the first resonance circuit 140 connected to the first probe 110 and the determination circuit 250 receives the first electrical signal having a first resonant frequency ca at step S520.

A second AC signal is applied to the second resonance circuit 240 by the second oscillator 247 at step S512. The operation of the second oscillator 247 or the operation of applying the second AC signal may be controlled by the control unit/controller/processor (not shown).

Due to the application of the second AC signal, a second electrical signal is formed in the second resonance circuit 240 and the determination circuit 250 receives the second electrical signal having a second resonant frequency $\omega 2$ at step S522. Steps S512 and S522 may be performed in parallel with steps S510 and S520.

The determination circuit 250 having received the first electrical signal and the second electrical signal detects the difference between the first resonant frequency $\omega 1$ and the second resonant frequency $\omega 2$ at step S530. The determination circuit 250 determines whether the moisture content contained in the soil located between the pair of first electrodes 111 and 112 of the first probe 110 has a significant value based on the difference between the first resonant frequency $\omega 1$ and the second resonant frequency $\omega 2$ at step S540.

When the determination circuit 250 does not determine that the moisture content contained in the soil located between the pair of first electrodes 111 and 112 of the first probe 110 has a significant value, the current process is terminated. If necessary, step S510 may be repeated again after a predetermined period of time has elapsed or when a predetermined condition is satisfied.

When the determination circuit 250 determines that the moisture content contained in the soil located between the pair of first electrodes 111 and 112 of the first probe 110 has a significant value, the determination circuit 250 determines the moisture content contained in the soil from the first probe 110 based on the difference between the first resonant frequency $\omega 1$ and the second resonant frequency $\omega 2$ at step S550.

Figure 6:
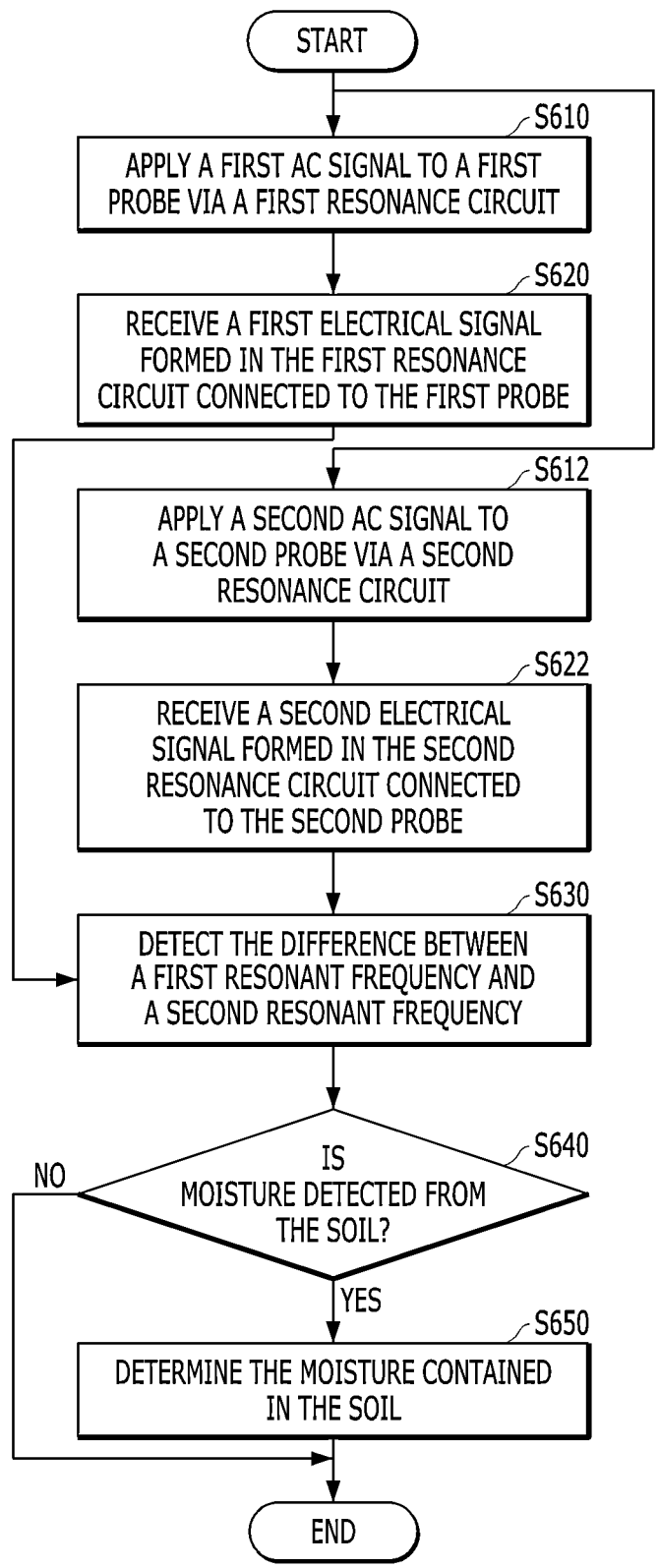
FIG. 6 is an operational flowchart showing a method of sensing moisture contained in the soil according to an embodiment of the present invention.

FIG. 6 is an operational flowchart showing a method of sensing moisture contained in the soil according to an embodiment of the present invention. The soil moisture sensing method of the present invention may be performed by the soil moisture sensors 100, 200, and 300 of FIGS. 1 to 4 or the controller/controller/processor (not shown) therein.

Referring to FIG. 6, a first AC signal is applied to the first probe 110 by the first oscillator 147 via the first resonance circuit 140 at step S610. Furthermore, the determination circuit 250 receives a first electrical signal formed in the first resonance circuit 140 connected to the first probe 110 and having a first resonant frequency ω1 at step S620.

A second AC signal is applied to the second probe 210 by the second oscillator 247 via the second resonance circuit 240 at step S612. In addition, the determination circuit 250 receives a second electrical signal formed in the second resonance circuit 240 connected to the second probe 210 and having a second resonant frequency ω2 at step S622. Steps S612 and S622 may be performed in parallel with steps S610 and S620.

In addition, the determination circuit 250 detects the difference between the first resonant frequency ω1 of the first electrical signal and the second resonant frequency ω2 of the second electrical signal at step S630.

The determination circuit 250 determines whether the moisture contained in the soil located between the pair of first electrodes 111 and 112 of the first probe 110 has a significant value based on the difference between the first resonant frequency ω1 and the second resonant frequency ω2 at step S640.

When the determination circuit 250 does not determine that the moisture contained in the soil located between the pair of first electrodes 111 and 112 of the first probe 110 has a significant value, the current process is terminated. If necessary, step S610 may be repeated again after a predetermined period of time has elapsed or when a predetermined condition is satisfied.

When the determination circuit 250 determines that the moisture contained in the soil located between the pair of first electrodes 111 and 112 of the first probe 110 has a significant value, the determination circuit 250 determines the moisture content contained in the soil based on the difference between the first resonant frequency ω1 from the first probe 110 and the second resonant frequency ω2, which is a reference resonant frequency, for the surface layer of the soil from the second probe 210 at step S650.

Figure 7:
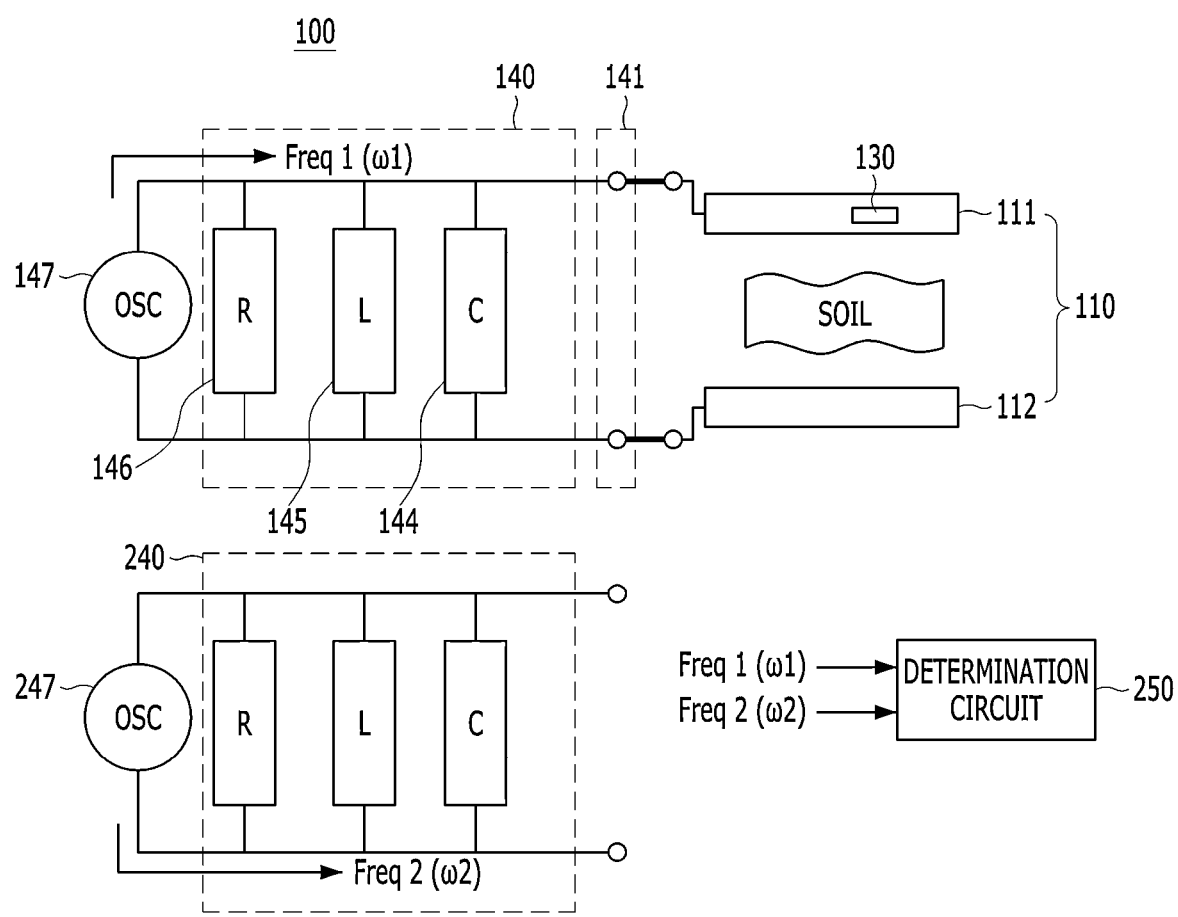
FIG. 7 is a diagram showing a soil moisture sensor according to an embodiment of the present invention.

FIG. 7 is a diagram showing a soil moisture sensor according to an embodiment of the present invention.

Since the first resonance circuit 140, first ports 141, first oscillator 147, second resonance circuit 240, second ports 241, second oscillator 247, and first probe 110 of FIG. 7 have been sufficiently described based on the items shown in FIG. 1, redundant descriptions thereof will be omitted. The descriptions of the operation of the determination circuit 250 of FIG. 7 that is very similar to those of the operation of the determination circuit 250 of FIG. 1 will be omitted.

The soil moisture sensor 100 of FIG. 7 may further include a temperature sensor 130 coupled to any one of the pair of first electrodes 111 and 112 of the first probe 110. In the case where the first probe 110 is inserted into the soil, when the first resonant frequency ω1 of the first resonance circuit 140 changes due to the composition of the soil, the temperature sensor 130 may measure the temperature of the soil.

As described above, the relative permittivity of vacuum is always maintained at 1 regardless of a change in temperature, but the permittivity of water decreases as the temperature increases. Accordingly, as the moisture content contained in the soil increases at a constant temperature, the permittivity constant of the soil will increase, and thus the capacitance of the soil will increase. When the temperature changes, the permittivity of water will change accordingly, and thus it is necessary to compensate the moisture content contained in the soil based on the change in temperature.

Therefore, the determination circuit 250 may generate a first determination value for the moisture in the soil based on the first resonant frequency ω1 and the second resonant frequency ω2, which is a reference resonant frequency, and may generate a second determination value for the moisture in the soil by compensating the first determination value based on the temperature measured by the temperature sensor 130.

It may also be understood that the determination circuit 250 detects a quantitative change in the first resonant frequency ω11. The determination circuit 250 may generate the first determination value for the moisture of the soil based on the quantitative change in the first resonant frequency ω1, and may generate the second determination value for the moisture in the soil by compensating the first determination value based on the temperature measured by the temperature sensor 130. More specifically, the determination circuit 250 may generate the first determination value for the moisture in the soil based on the first resonant frequency ω1 and the second resonant frequency ω2, which is a reference resonant frequency, and may generate the second determination value for the moisture in the soil by compensating the first determination value based on the temperature measured by the temperature sensor 130.

The first threshold value, the second threshold value, the third threshold value, or the fourth threshold value used by the determination circuit 250 is compared with the second determination value obtained through the compensation based on the temperature of the soil or a value proportional to the second determination value, so that quantified information such as the validity of the result of measurement of moisture in the soil and the range of the measured moisture content in the soil may be specified.

Although the temperature sensor 130 is coupled to any one 111 of the two first electrodes 111 and 112 in FIG. 7, this is merely an embodiment, and there may also be implemented an embodiment in which the temperature sensor 130 is coupled to each of the two first electrodes 111 and 112 and a representative value is selected based on measured values of the temperature sensors 130. In a simple example, a hole configured to come into contact with the soil is formed in the electrode 111, the temperature sensor 130 is disposed inside the hole, and a path through which the soil flows into the hole is formed such that the temperature sensor 130 can directly come into contact with the soil. A target whose temperature is measured by the temperature sensor 130 is the soil containing moisture, and may be the soil and moisture introduced into the hole.

A known temperature sensor may be utilized as the temperature sensor 130 in various manners. One of the widely known methods of measuring temperature is to use a negative temperature coefficient (NTC) material. Since values such as resistance will vary based on temperature, the temperature may be calculated by detecting a change in the electrical signal such as voltage or current by using this fact.

The determination circuit 250 may calculate the permittivity of water based on the measured temperature, and may calculate a compensated capacitance value based on a measured frequency shift and the temperature-compensated permittivity of water. The determination circuit 250 may calculate the moisture content or water content of the soil or a medium (a medium in which the crop grows) based on the compensated capacitance value.

In this case, the moisture content, the water content, and/or capacitance value may be given as a function of the temperature and the shift of a resonant frequency. Alternatively, the determination circuit 250 may calculate the moisture content or water content of the soil based on the temperature based on predetermined and pre-stored table information. The table information may store the temperature and information about relationships with other variables. For example, other variables that may be contrasted with temperature may include at least one of a moisture content, a capacitance value, a change in impedance, and the shift of a resonant frequency.

The method of operating a circuit according to an embodiment of the present invention may be implemented in the form of program instructions, and may then be recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, high-frequency signals are generated in the circuit having a capacitance formed in a probe for a soil moisture sensor using the soil as a medium and the circuit having a reference capacitance, respectively, frequencies for the high-frequency signals in the two circuits are measured and compared, and the moisture content in the soil is quantified, thereby enabling the moisture state of the soil to be more accurately and rapidly determined in real time.

Furthermore, according to the present invention, the soil moisture sensor may be used non-destructively and semi-permanently, and the stability of the solid moisture sensor may be ensured.

Furthermore, according to the present invention, when the determination circuit of the soil moisture sensor is fabricated using a single chip, the sensor circuit and the reference resonance circuit are disposed close to each other, and the same type of devices may be used for the fabrication, so that a measurement error attributable to semiconductor process variation may be reduced, thereby enabling the moisture content of the soil to be accurately determined in real time.

The soil moisture sensor according to the present invention may further include a temperature sensor in order to more accurately detect the moisture content of the soil, and may measure precise moisture content by compensating the moisture content of the soil based on the temperature sensor.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A soil moisture sensor comprising:
   a first probe including a pair of first electrodes extending in a first direction in order to penetrate into a soil;
   a first resonance circuit connected to the pair of first electrodes of the first probe through a pair of first ports, and configured such that a first alternating current (AC) signal is applied thereto;
   a second resonance circuit having a same impedance as the first resonance circuit, and configured such that a second AC signal having same characteristics as the first AC signal while being a reference AC signal is applied thereto; and
   a determination circuit configured to:
      receive a first electrical signal formed in the first resonance circuit;
      receive a second electrical signal formed in the second resonance circuit; and
      generate a first determination value for moisture in the soil based on a first resonant frequency of the first electrical signal and a second resonant frequency of the second electrical signal.

2. The soil moisture sensor of claim 1, wherein the determination circuit is further configured to:
   detect a quantitative change in the first resonant frequency of the first electrical signal formed in the first resonance circuit based on a capacitance formed between the pair of first electrodes by the moisture contained in the soil located between the pair of first electrodes; and
   generate the first determination value for the moisture contained in the soil based on the detected quantitative change in the first resonant frequency.

3. The soil moisture sensor of claim 1, wherein the determination circuit is further configured to:
   detect a difference between the second resonant frequency, which is a reference resonant frequency of the second electrical signal formed in the second resonance circuit under an influence of the second AC signal applied to the second resonance circuit, and the first resonant frequency; and
   generate the first determination value for the moisture contained in the soil based on the difference between the second resonant frequency and the first resonant frequency.

4. The soil moisture sensor of claim 3, wherein the determination circuit is further configured to:
   if the difference between the second resonant frequency and the first resonant frequency is equal to or larger than a first threshold value,
   consider that the first resonant frequency has caused a significant change; and
   determine that the first determination value is a valid value for the moisture contained in the soil.

5. The soil moisture sensor of claim 1, further comprising:
   a temperature sensor coupled to any one of the pair of first electrodes of the first probe,
   wherein the determination circuit is further configured to generate a second determination value for the moisture in the soil by compensating the first determination value based on a temperature measured by the temperature sensor.

6. The soil moisture sensor of claim 1, wherein the determination circuit comprises:
an operator circuit configured to obtain a difference between the first resonant frequency and the second resonant frequency;
a low-pass filter connected to an output terminal of the operator circuit, and configured to remove a high-frequency component; and
a time-to-digital converter connected to an output terminal of the low-pass filter, and configured to digitally count a frequency of a third frequency component signal corresponding to the difference between the first resonant frequency and the second resonant frequency.

7. The soil moisture sensor of claim 1, further comprising:
a second probe including a pair of second electrodes formed to come into contact with or penetrate into a surface layer of the soil,
wherein the second resonance circuit is connected to the pair of second electrodes included in the second probe via a pair of second ports.

8. The soil moisture sensor of claim 7, wherein the determination circuit is further configured to determine the moisture contained in the soil based on a quantitative difference between the second resonant frequency of the second electrical signal, formed in the second resonance circuit based on a second capacitance formed between the pair of second electrodes, and the first resonant frequency.

9. A soil moisture sensing method comprising:
applying, by a first oscillator, a first alternating current (AC) signal via a first resonance circuit that is connected to a pair of first electrodes of a first probe including the pair of first electrodes extending in a first direction in order to penetrate into the soil through a pair of first ports;
applying, by a second oscillator having same characteristics as the first oscillator, a second AC signal, which is a reference AC signal, to a second resonance circuit having a same impedance as the first resonance circuit;
receiving, by a determination circuit, a first electrical signal formed in the first probe and the first resonance circuit under an influence of the first AC signal;
receiving, by the determination circuit, a second electrical signal formed in the second resonance circuit under an influence of the second AC signal applied to the second resonance circuit; and
generating, by the determination circuit, a first determination value for moisture contained in a soil located between the pair of first electrodes of the first probe based on a first resonant frequency of the first electrical signal and a second resonant frequency of the second electrical signal.

10. The soil moisture sensing method of claim 9, wherein the generating comprises:
detecting a quantitative change in the first resonant frequency of the first electrical signal formed in the first resonance circuit based on a capacitance formed between the pair of first electrodes by the moisture contained in the soil located between the pair of first electrodes; and
generating the first determination value for the moisture contained in the soil based on the detected quantitative change in the first resonant frequency.

11. The soil moisture sensing method of claim 9, further comprising:
detecting, by the determination circuit, a difference between the first resonant frequency and the second resonant frequency,
wherein the generating comprises generating the first determination value for the moisture contained in the soil located between the pair of first electrodes of the first probe based on the difference between the first resonant frequency and the second resonant frequency.

12. The soil moisture sensing method of claim 9, further comprising:
measuring, by a temperature sensor coupled to any one of the pair of first electrodes of the first probe, a temperature of the soil; and
generating a second determination value for the moisture in the soil by compensating the first determination value based on the temperature measured by the temperature sensor.

13. The soil moisture sensing method of claim 9, further comprising:
applying, by the second oscillator, the second AC signal to a second probe, connected to the second resonance circuit through a pair of second ports and including a pair of second electrodes formed to come into contact with or penetrate into a surface layer of the soil, via the pair of second ports.

* * * * *